United States Patent
Fabo et al.

(10) Patent No.: US 8,545,468 B2
(45) Date of Patent: Oct. 1, 2013

(54) COMPONENT FOR FORMING A SEAL AROUND AN OPENING IN THE SKIN

(75) Inventors: Tomas Fabo, Molnlycke (SE); Bengt Soderstrom, Molndal (SE); Anna Svensby, Gothenburg (SE)

(73) Assignee: Mölnlycke Health Care AB, Göteborg (SE)

( * ) Notice: Subject to any disclaimer, the term of this patent is extended or adjusted under 35 U.S.C. 154(b) by 857 days.

(21) Appl. No.: 11/794,942

(22) PCT Filed: Jan. 9, 2006

(86) PCT No.: PCT/SE2006/000024
§ 371 (c)(1),
(2), (4) Date: Sep. 18, 2007

(87) PCT Pub. No.: WO2006/075949
PCT Pub. Date: Jul. 20, 2006

(65) Prior Publication Data
US 2008/0097361 A1     Apr. 24, 2008

(30) Foreign Application Priority Data
Jan. 11, 2005  (SE) .................................... 0500063

(51) Int. Cl.
*A61F 5/448*  (2006.01)
(52) U.S. Cl.
USPC ......................................... 604/338; 604/332
(58) Field of Classification Search
USPC ................... 604/332, 336–344; 602/42, 52, 602/54, 69; 427/2.31
See application file for complete search history.

(56) References Cited

U.S. PATENT DOCUMENTS

| | | | | |
|---|---|---|---|---|
| 3,128,030 A | * | 4/1964 | Davies | 229/406 |
| 3,908,658 A | | 9/1975 | Marsan | |
| 4,219,023 A | * | 8/1980 | Galindo | 604/344 |
| 4,231,369 A | | 11/1980 | Sorensen et al. | |
| 4,621,029 A | | 11/1986 | Kawaguchi | |
| 4,775,374 A | * | 10/1988 | Cilento et al. | 604/344 |
| 5,074,852 A | * | 12/1991 | Castellana et al. | 604/336 |
| 5,160,330 A | * | 11/1992 | Cross | 604/339 |
| 5,545,154 A | * | 8/1996 | Oberholtzer | 604/336 |
| 5,951,533 A | * | 9/1999 | Freeman | 604/338 |
| 6,387,082 B1 | | 5/2002 | Freeman | |
| 6,846,508 B1 | * | 1/2005 | Colas et al. | 427/2.31 |
| 7,192,420 B2 | * | 3/2007 | Whiteford | 604/336 |
| 2006/0228318 A1 | | 10/2006 | Fabo | |

FOREIGN PATENT DOCUMENTS

| | | |
|---|---|---|
| EP | 1 424 088 A1 | 6/2004 |
| JP | 10-506023 | 6/1998 |
| JP | 2002-516152 | 6/2002 |
| SE | 526906 | 11/2005 |

(Continued)

OTHER PUBLICATIONS

Swedish Patent Office Action, dated Nov. 24, 2008 and issued in corresponding Swedish Patent Application No. 0500063-3. CN Office Action dated May 27, 2010 from CN200680001721.8.
Notice of Reasons for Rejection in Japanese Application No. 2007-550334, dated Aug. 31, 2010.

(Continued)

*Primary Examiner* — Susan Su
(74) *Attorney, Agent, or Firm* — Ballard Spahr LLP

(57) ABSTRACT

A component is suitable for protecting skin around an opening in the skin or around a stoma. The component can be formed from a carrier (2; 2') that is enclosed between layers of soft and skin-compatible adhesive (3; 3'), and the adhesive has a softness of 8-22 mm. The adherence of the adhesive to dry skin can be 0.2-3 N/25 mm.

21 Claims, 3 Drawing Sheets

(56) References Cited

FOREIGN PATENT DOCUMENTS

| WO | WO 96/03167 | 2/1996 |
|---|---|---|
| WO | 98/53778 | 12/1998 |
| WO | WO-99/61077 A1 | 12/1999 |
| WO | WO 99/61078 | 12/1999 |
| WO | 03/079919 | 10/2003 |
| WO | 2004/108175 | 12/2004 |
| WO | WO 2004/108175 | 12/2004 |

OTHER PUBLICATIONS

Thomas, X. et al., "Adhesive Technologies for Attaching Medical Devices to the Skin," Medical Device Technology, Sep. 2004, pp. 1-4.
Notice of Opposition to a European Patent, filed on Mar. 29, 2012, European Patent No. 1838257 granted Jun. 29, 2011, "Component for Forming a Seal Around an Opening in the Skin," Proprietor—Mölnlycke Heath Care AB, pp. 1-17.

\* cited by examiner

COMPONENT FOR FORMING A SEAL AROUND AN OPENING IN THE SKIN

TECHNICAL FIELD

The present invention relates to a component for forming a seal around an opening in the skin, for example a stoma.

BACKGROUND TO THE INVENTION

Since the end of the 1970s, hydrocolloid-based adhesives have been used in systems for fastening stoma bags to patients who have undergone an ostomy procedure. Such systems function well in many cases, but it is not uncommon for skin irritation or skin damage to occur in the area around the stoma. This applies particularly to the area nearest to the stoma, which area is difficult to protect since the aim is to avoid contact between the hydrocolloid plate and the mucous membrane at the base of the stoma, i.e. the part of the stoma protruding from the body. To improve the leaktightness in the area around a stoma, it is known to use plastic sealing compositions and various types of pastes which, for example, are available in tubes.

The present invention aims to provide a component which improves the leaktightness around a stoma, additionally contributes to making it easier to fasten stoma bags, and eliminates or at least to a large extent reduces the risk of skin irritation or skin damage occurring in the area around the stoma of a patient who has undergone an ostomy procedure.

DISCLOSURE OF THE INVENTION

According to the invention, these aims are achieved by a component for forming a seal around an opening in the skin, characterized in that it comprises a carrier which is enclosed between layers of soft and skin-compatible adhesive. By virtue of the fact that the adhesive is very soft, it can penetrate down into all irregularities in the skin so that fluid, which may leak from the opening, cannot escape across the skin. The component according to the invention is also very shapeable, which means that the edge of the opening in the component can be applied very close to a stoma without risk of irritation or bleeding of the mucous membrane at the base of the stoma. The component according to the invention is in principle hydrophobic, although hydrophilic additives are conceivable, and it does not affect this mucous membrane to the same extent as a hydrophilic component. The component according to the invention can also be stretched together with the skin so that there is considerably less risk of shearing between skin and adhesive, which shearing can give rise to mechanical damage to the skin. A further advantage of the component according to the invention is that it is adherent to skin and can be reapplied after removal from skin because it does not to any appreciable extent pull off skin cells with it during removal, which would otherwise reduce the adherence surface of the component available for reapplication. Hydrocolloid material, when removed, pulls off so many skin cells that its surface area available for reapplication is considerably decreased after removal. Components according to the invention do not pull off hairs either, and there is therefore no risk of inflammation in the hair follicles resulting from use of such components. Therefore, skin irritation as a consequence of shaving can also be avoided using components according to the invention. Components according to the invention can also be made transparent, which means that it is easier to place the component in the correct place than if it were non-transparent, and easier to monitor the state of the skin without having to detach the component. The component is intended for use around stomas of various types, for example colostomies, ileostomies and urostomies, but it can also be used for protecting and forming a seal around other openings in the skin, for example around tracheostomies, catheters, tubes and other items of medical equipment which pass through the skin.

In a preferred embodiment, the adherence of the adhesive to dry skin is 0.2-3 N/25 mm, preferably 1-2.5 N/25 mm. The component can have an elongate shape or can be circular. In one variant, the carrier comprises fibre material, for example a string, or is a thin-woven or nonwoven fabric. In another variant, the carrier comprises one or more layers of plastic film. The carrier can advantageously be provided with holes, and the adhesive then extends through the holes in the carrier. The adhesive preferably comprises a soft and skin-compatible silicone elastomer. The thickness of the component is 0.2-20 mm, preferably 0.5-10 mm, and the adhesive has a softness of 8-22 mm, preferably 12-17 mm. A layer of release material which is removed prior to use of the component is arranged on opposite sides of the component.

One or more skin-care substances can also be admixed to the adhesive.

BRIEF DESCRIPTION OF THE DRAWINGS

The invention will now be described with reference to the attached figures where.

DESCRIPTION OF EMBODIMENTS

Figure 1:
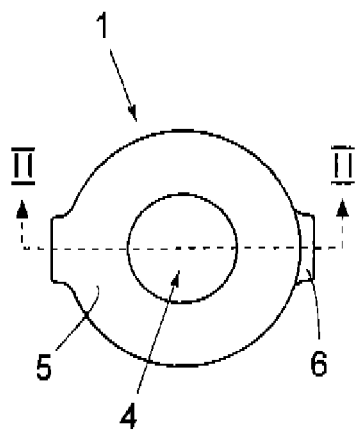
FIG. 1 shows a schematic plan view of a component according to a first preferred embodiment of the invention.
Figure 2:
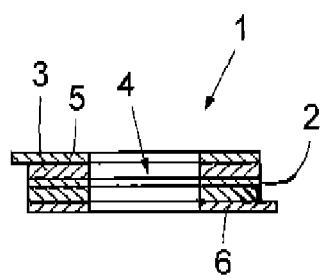
FIG. 2 shows a cross section along the line II-II in FIG. 1.

FIGS. 1 and 2 show a first embodiment of a component 1 for forming a seal around a stoma. In the embodiment shown, the component 1 is circular and comprises a carrier 2, for example a net of textile or synthetic fibres, an open-cell polymer foam, for example polyurethane, or a perforated plastic film, enclosed in an adhesive layer 3 of a soft and skin-compatible adhesive, for example a silicone elastomer, which adheres to skin. As will be seen from the figure, the adhesive extends through the meshes or holes in the carrier 2. The carrier material can be made up of fibres of polyamide or polyester or of perforated polyurethane elastomer film. The size of the holes in the carrier can vary to a large extent and it is possible to use thin-woven textiles or even nonwoven material as the carrier, as long as the materials are permeable enough to allow the adhesive to penetrate through the material during manufacture. Knitted textiles can also function as the carrier material.

The component 1 also has a through-opening 4. Before use, the adhesive layer 3 is protected by release layers 5, 6 which, when silicone elastomer is used as adhesive, can comprise polyethylene or otherwise a silicone-coated release paper of conventional type, or any other known material which is used as release layers and is arranged on the top and bottom faces of the component. To make detachment of the release layers 5, 6 easier when these are to be removed at the time of application of the component 1, these have a part which extends laterally outside the component 1.

The adhesive layer 3 is advantageously made up of a silicone composition which, after mixing together, crosslinks to a soft elastomer. Specially suitable are RTV (room temperature vulcanizing) silicone systems which are addition-curing and which can be crosslinked at moderate temperatures. RTV silicones can be made soft, pliable and self-adhering.

Examples of RTV addition-curing silicone systems are given in EP 0 300 620 A1 which describes what it calls "gel-forming compositions" comprising an alkenyl-substituted polydiorganosiloxane, an organosiloxane containing hydrogen atoms bound to some of the silicone atoms, and a platinum catalyst.

An example of a commercially available RTV silicone system is Wacker SILGEL 612 (silicone adhesive) from Wacker-Chemie GmbH, Munich, Germany. This is a two-component system. By varying the proportions between the two components A:B from 1.0:0.7 to 1.0:1.3, it is possible to vary the softness and level of adherence of the elastomer that is formed.

Examples of other soft silicone elastomers which adhere to dry skin are NUSIL MED 6340, NUSIL MED3-6300, NUSIL MED12-6300 (silicone elastomers) from NuSil Technology, Carpinteria, Ga., USA, and Dow Corning 7-9800 from Dow Corning Corporation, Midland, USA.

The silicone elastomer layer 3 can also comprise a number of additives for different purposes, for example paraffin or ZnO for controlling the rheology, urea for reducing the drying-out of the skin, anti-inflammatory preparations such as hydrocortisone, antimicrobial preparations, buffering additives for lowering the pH value of pH-neutral water to 3.5-6.0, preferably to 4.5-5.8 and particularly preferably to 4.9-5.5. Such pH-buffering additives are described in WO 02/28447 A1, to which document reference may be made for further details.

Figure 3:
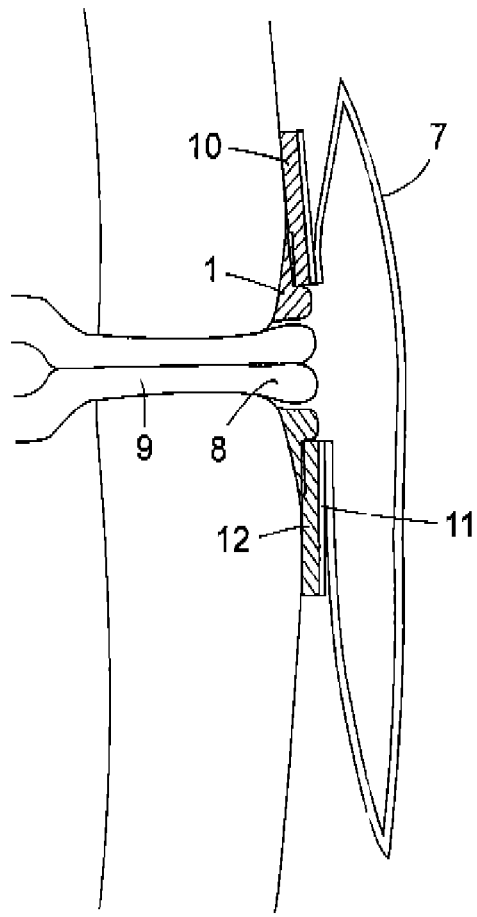
FIG. 3 shows a schematic view of a fastening system for a stoma bag in which a component according to FIG. 1 is included.

FIG. 3 shows a use of the component 1 in a system for fastening a stoma bandage 7 of conventional construction around a patient's stoma 8. The area 8 is that part of a patient's intestine 9 extending outside the patient's body, as is shown schematically in FIG. 3. The stoma bandage 7 comprises a bag part with an opening, and a fastening part 10 secured to the bag part around this opening. The fastening part 10 comprises a plastic layer 11 coated with an adhesive layer 12 of a hydrocolloid. A component 1 according to the invention is also fitted close to the stoma, and its layer 3 of silicone elastomer is secured to the skin around the stoma 8. The adhesive layer 12 of the fastening part 10 of the stoma bag 7 is secured to the component 1 in the area nearest to the stoma and is secured to the patient's skin in the area outside the component 1.

Since the silicone elastomer is very soft and has low surface energy, it wets very well to the skin, i.e. it spreads out in the irregularities of the skin and creates a large contact surface between skin and silicone elastomer. This large contact surface helps the silicone elastomer fasten effectively to the skin despite the fact that the silicone elastomer's binding force to skin is not inherently great. The adherence force represents a measure of the energy that is needed to separate/pull off the adhesive layer from skin. A contributory factor explaining why considerable energy and thus a considerable pulling-off force is needed to remove silicone elastomers from the skin, despite the relatively weak binding force, is that a great deal of energy is expended in stretching the soft silicone elastomer before it detaches from the skin. The softer and thicker the layers of silicone elastomer, the more force/energy is needed for removing the elastomer from the skin.

If a harder adhesive is used, a stronger binding force is needed to ensure that the pulling-off force will be as great as for a softer adhesive easily. A strong binding force between skin and adhesive leads to skin cells being pulled away from the skin when the adhesive is being removed.

Another disadvantage of harder adhesives is that these may spread outwards over the course of time and thus increase the contact surface with the skin, which has the result that the pulling-off force increases with time, which can mean that these adhesives eventually become difficult to remove from the skin. In contrast to harder adhesives such as hydrocolloids, softer adhesives such as silicone elastomers achieve their full force of adherence all at once so that their pulling-off force remains constant over time. The adhesives to be used in a component according to the invention have a softness of 8-22 mm while the hydrocolloid adhesives present in conventionally used stoma plates only have a softness of 2-5 mm.

Since, as has already been mentioned, the silicone elastomer in the layer 3 of the component 1 is very soft, it can penetrate down into all the irregularities in the skin, so that fluid which escapes from the stoma opening cannot spread out across the skin. The plates of hydrocolloid material 12 which are presently used in fastening systems for stoma bags are relatively stiff and have to be kept at a distance from the stoma so as not to come into contact with the latter and thereby irritate or damage the mucous membrane on the base of the stoma 8. For this reason, it is expedient to arrange a soft component according to the invention nearest to the stoma. The component 1 ensures a good seal with the skin so that fluid which is excreted from the stoma cannot run under the component. Moreover, the component is shapeable such that the edge of the opening of the component can be easily adapted to the shape of the stoma and can thus be applied very close to the stoma. The component according to the described embodiment also maintains its integrity upon contact with fluid. In this context it should be noted that if the opening of the component 1 is too small, it can be made larger by punching or cutting in order to adapt its size to the stoma. Conventional fastening arrangements for stoma bags are often provided with cutting marks, for example in the form of helical lines, to make this kind of adaptation easier. Such adaptation of size is important for ensuring that the smallest possible area of skin around the stoma comes into contact with the intestinal content collected in the stoma bag. As has already been mentioned, the shapeability of the component 1 means it is easy to finely adjust the shape of the opening 4 so that this coincides with the cross-sectional shape of the stoma 8, which may deviate from a circular shape.

Moreover, the component 1 according to the invention can be stretched together with the skin, such that there is a significantly reduced risk of shearing between skin and adhesive, which shearing may give rise to mechanical damage of the skin. A further advantage of the component according to the invention is that it can be reapplied after removal from the skin because it does not to any appreciable extent pull off skin cells with it when removed, which would otherwise reduce the component's adhesive surface area available for reapplication. Hydrocolloid material pulls off so many skin cells with it that its surface available for reapplication decreases considerably after removal. It is thus possible to adjust the position of the component 1 in relation to the stoma if so required. The component 1 according to the invention does not pull off any hairs either, and the use of such components does not therefore pose any risk of inflammation in the hair follicles. Irritation of the skin as a consequence of repeated shaving of the area nearest the stoma can thus also be avoided when using components according to the invention. Components according to the invention can also be made transparent, which means that it is possible to monitor the state of the skin without having to detach the component before a new stoma bag is to be fitted.

Figure 6:
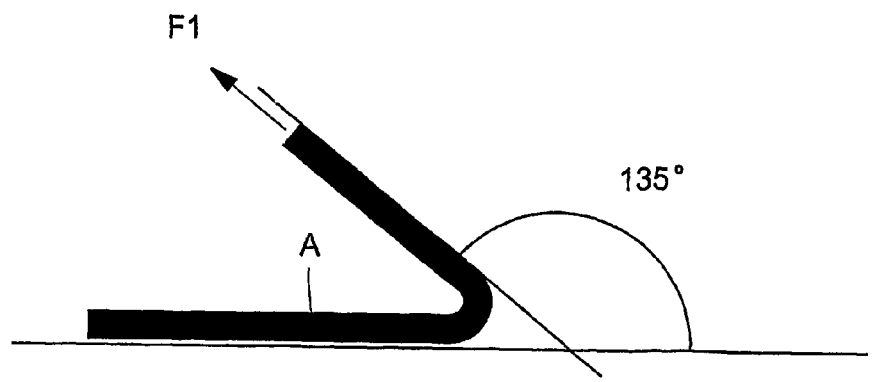
FIG. 6 illustrates measurement of the force of adherence to skin.

Since the properties of the skin vary from person to person, the ability of the adhesive coating 3 to adhere to skin of course also varies for different patients. The force of adherence is also dependent on the thickness of the adhesive and the mechanical properties of the carrier. The standard methods for measuring adherence which are employed at the present time make use of plates of various types, for example of steel or glass, and do not give values relevant for measuring adherence to skin. The skin adherence values of an adhesive which are specified below will be measured by a method which is illustrated in FIG. 6 and which has been developed by the Applicant. Strips A of a carrier material, a polyurethane film with thickness 25±5 micrometers, coated with the adhesive whose force is to be measured, and with a width of 25 mm, are placed on the skin of the back of at least ten healthy subjects of different age and sex and are allowed to remain on the skin for two minutes. The weight per unit area of the adhesive layer will be 100 g/m². The strips A are thereafter removed at a speed of 25 mm/sec and the pulling-off force F1 is measured. The pulling-off angle, that is to say the obtuse angle formed between the skin surface and the pulled-off part of the strip, will be 135°. The measured skin adherence force of the adhesive is represented by the mean value of the measured force F1. Adhesives that can be used in components according to the invention will have an adherence force according to this method of 0.2-3 N/25 mm. The adherence force is preferably 1-2.5 N/25 mm.

Figure 7:
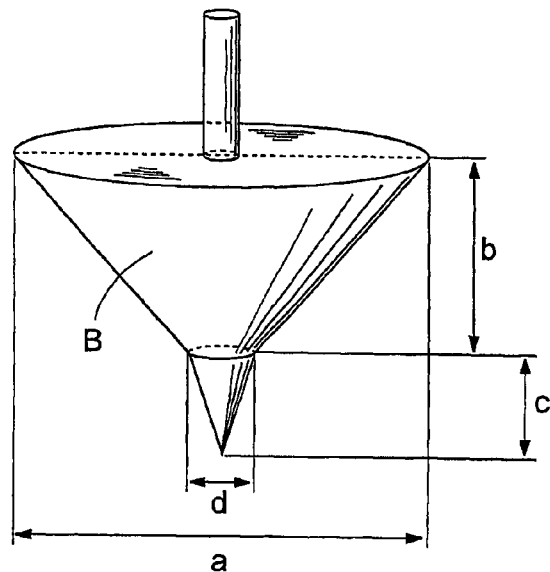
FIG. 7 shows a cone used for measuring softness.
Figure 8:
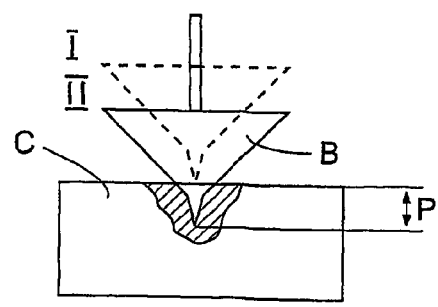
FIG. 8 illustrates a method for measuring softness.

Adhesive according to the invention will have a softness exceeding 8 mm measured by a method based on ASTM D 937 and ASTM D 51580. Certain modifications, which are set out below, have been made to the method. FIGS. 7 and 8 illustrate this modified method of measuring softness of an adhesive by allowing a cone B with a weight of 62.5 g to penetrate by gravity into a 30-mm thick test specimen C of the adhesive whose softness is to be determined. The test specimen is obtained by a cylindrical glass container with internal diameter 60 mm and an inner height of 35-40 mm being filled with adhesive up to a height of 30 mm. For a silicone elastomer, non-cured silicone prepolymer is introduced into the container and is then crosslinked to an elastomer in the glass cylinder. The cone used is shown in FIG. 7 and has the following dimensions: a=65 mm, b=30 mm, c=15 mm and d=8.5 mm. When carrying out the method for measuring softness, the cone B is first lowered to a position I which is shown by broken lines in FIG. 8 and in which the tip of the cone just touches the surface of the test specimen C. The cone B is then released so that it is allowed to penetrate by force of gravity down into the test specimen C. The number of mm the tip of the cone B has penetrated into the test specimen C after 5 seconds is measured and represents the penetration value P, which is higher the softer the test specimen. The penetration value P represents the measure of softness used in the present invention. When carrying out the method, a Penetrometer PNR 10 from Sommer & Runge KG, Germany was used. The softness of the adhesives used in the component 1 is preferably 8-22 mm, especially preferably 12-17 mm.

To ensure that only a low application force is needed for applying the component 1 according to the present invention, the softness of the soft and skin-compatible adhesive used is preferably greater than 12 mm. The softer an adhesive, the more rapidly it spreads into any irregularities in the skin, which means that the component 1 according to the invention is leakproof directly after application.

Another important property of the component 1 according to the invention is that the adherence force of the soft, skin-compatible adhesives used does not change with time, or changes only to a small extent with time, during the period the component is fastened to the skin.

The component 1 is also sterilizable, which means that it can be delivered in sterile packaging if so desired.

Figure 4:
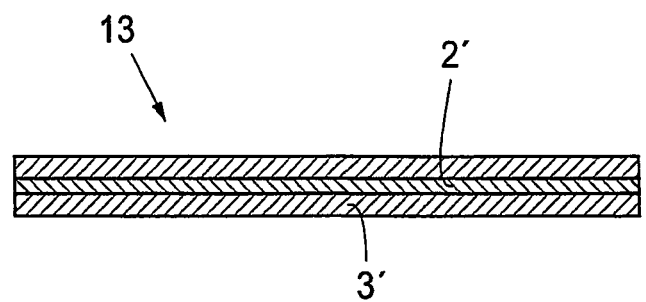
FIG. 4 shows a schematic cross-sectional view of a component according to a second preferred embodiment of the invention.
Figure 5:
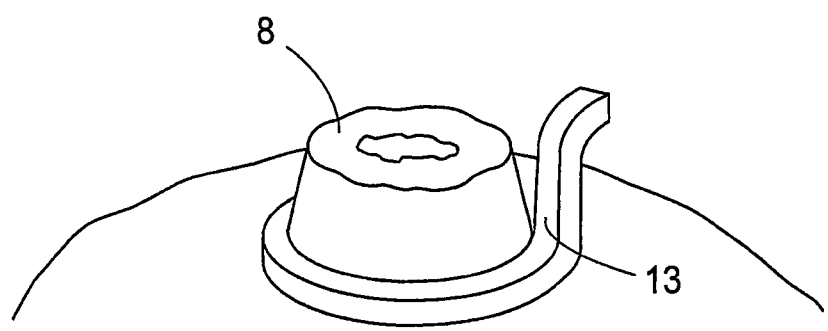
FIG. 5 shows a schematic view of a component according to the embodiment in FIG. 4 applied around a stoma.

FIGS. 4 and 5 show a second preferred embodiment of a component 13 according to the invention. This component has the same structure as the component 1 described with reference to FIGS. 1-3 but differs from this in being elongate rather than circular. The component is thus formed from an elongate carrier 2' of the same type as the carrier 2 in the embodiment according to FIGS. 1-3, enclosed in a silicone elastomer 3' of the same type as the silicone elastomer in the embodiment according to FIGS. 1-3. FIG. 5 shows schematically how the component 13 is applied around a stoma 8' by being wound round the latter. The length of the component 13 is adapted expediently by cutting before the release layers are removed, so that the cut edge comes to bear against the edge applied first. Since the silicone elastomer adheres to itself, a tight joint between said edges can be easily obtained. In cases where the skin is pulled into the area around a stoma so that a depression is formed, it may be expedient to wind the component 13 more than once round the stoma so that the fastening arrangement of the stoma bag will bear and fasten against the component such that fluid will not be able to flow across the top face of the component 13 between the latter and the overlying hydrocolloid plate of this fastening arrangement.

The adhesives used in the invention also adhere to the stoma bandage with which they are intended to cooperate, which fact further contributes to ensuring leaktightness. Examples of adhesives other than silicone elastomers that are able to function as soft, skin-compatible adhesives according to the invention are certain hot-melt adhesives, for example of the type described in U.S. Pat. No. 5,559,165.

In the embodiments shown here, the carriers extend out to the edges of the component. This is not essential and not always desirable. The function of the carrier is to limit the stretching and shapeability of the component and to bind the soft adhesive so that the whole component can be removed in one piece. As has already been mentioned, the use of soft adhesive means there is considerably less risk of the component according to the invention irritating or damaging the mucous membrane when in contact with the latter. It is therefore advantageous if the adhesive layer extends round the edges of the carrier.

In this connection, it should be noted that the pastes and plastic sealing compositions used today for forming a seal around stomas are more akin to viscous fluids, which cannot be removed in one piece.

The described embodiments can of course be modified without departing from the scope of the invention. For example, the component 1 can have an outer shape other than circular, and the component 13 can have a cross section other than rectangular, for example it can have the shape of a right-angled triangle. The component 1 can also be profiled, for example can be thicker in the inner edge of the opening 4. In the embodiments, the components are shown with just one carrier, but it is of course possible to have several carriers enclosed between layers of adhesive, particularly in the case of thick components. Moreover, the release layers can be configured such that they extend also over the edges of these components, at least the outer edges, such that no part of the tacky adhesive is exposed externally before use. The invention is therefore not limited by the content of the attached patent claims.

The invention claimed is:

1. A component for protecting skin around a stoma and in combination with a stoma bandage, comprising:
   a carrier which is enclosed between layers of skin-compatible adhesive, the adhesive comprising silicone elastomer and having a softness of 8-22 mm,
   wherein the stoma bandage comprises:
      a bag part with an opening,
      a fastening part including an adhesive layer secured to the bag part around the opening, the fastening part being secured to the component in an area near the stoma after application of the component around the stoma,
   and wherein the component is separate from the stoma bandage.

2. The component according to claim 1, wherein the carrier comprises one or more layers of plastic film.

3. The component according to claim 1, wherein the carrier is provided with holes, and the adhesive extends through the holes in the carrier.

4. The component according to claim 1, wherein a thickness of the component is 0.2-20 mm.

5. The component according to claim 1, wherein the adhesive has a softness of 12-17 mm.

6. The component according to claim 1, wherein a layer of release material which is removed prior to use of the component is arranged on opposite sides of the component.

7. The component according to claim 1, wherein an adherence of the adhesive to dry skin is 1-2.5 N/25 mm.

8. The component according to claim 1, wherein a thickness of the component is 0.5-10 mm.

9. The component according to claim 1, wherein the component has a smaller area than an area of the adhesive layer of the stoma bandage.

10. The component according to claim 1, wherein an adherence of the adhesive to dry skin is 0.2-3 N/25 mm.

11. The component according to claim 10, wherein said component has an elongate shape.

12. The component according to claim 10, wherein said component is circular.

13. The component according to claim 10, wherein the carrier comprises fibre material.

14. The component according to claim 10, wherein the carrier comprises one or more layers of plastic film.

15. The component according to claim 10, wherein the carrier is provided with holes, and the adhesive extends through the holes in the carrier.

16. The component according to claim 10, wherein the adhesive has a softness of 12-17 mm.

17. The component according to claim 10, wherein a layer of release material which is removed prior to use of the component is arranged on opposite sides of the component.

18. The component according to claim 1, wherein the carrier comprises fibre material.

19. The component according to claim 18, wherein the carrier comprises a string.

20. A component, comprising:
   a carrier (2; 2') which is enclosed between layers of soft and skin-compatible adhesive (3; 3'), the adhesive comprising a silicone elastomer,
   wherein the adhesive has a softness of 8-22 mm, and
   the component forms a protective bandage around a stoma,
   and the component is in combination with a stoma bandage comprising:
      a bag part with an opening,
      a fastening part including an adhesive layer secured to the bag part around the opening, the fastening part being secured to the component in an area near the stoma after application of the component around the stoma,
   and wherein the component is separate from the stoma bandage.

21. The component according to claim 20, wherein the component has a smaller area than an area of the adhesive layer of the stoma bandage.

* * * * *

UNITED STATES PATENT AND TRADEMARK OFFICE
CERTIFICATE OF CORRECTION

PATENT NO.        : 8,545,468 B2                                         Page 1 of 1
APPLICATION NO.   : 11/794942
DATED             : October 1, 2013
INVENTOR(S)       : Fabo et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 690 days.

Signed and Sealed this
Fifteenth Day of September, 2015

Michelle K. Lee
*Director of the United States Patent and Trademark Office*